Figure 1B:
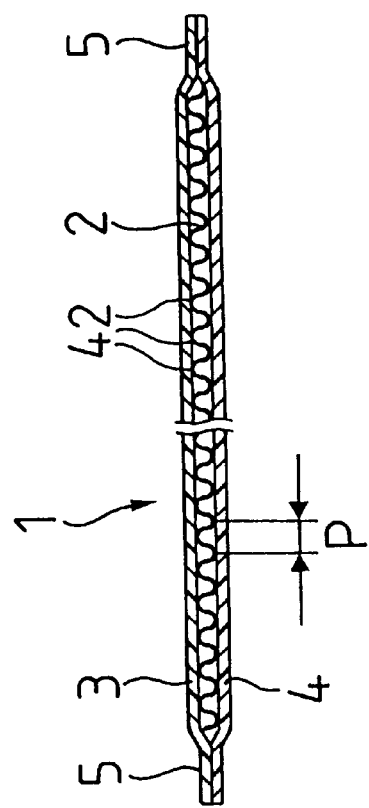

United States Patent [19]
Bolla et al.

[11] Patent Number: 6,039,706
[45] Date of Patent: Mar. 21, 2000

[54] MEDICAL SPLINT, METAL SHEET FOR SUCH A SPLINT AND ITS USE

[75] Inventors: Kalman Bolla; Orsolya Bolla, both of Neuhausen am Rheinfall, Switzerland

[73] Assignee: Chrisofix AG, Schaffhausen, Switzerland

[21] Appl. No.: 09/077,958

[22] PCT Filed: Dec. 19, 1996

[86] PCT No.: PCT/CH96/00450

§ 371 Date: Aug. 5, 1998

§ 102(e) Date: Aug. 5, 1998

[87] PCT Pub. No.: WO97/22312

PCT Pub. Date: Jun. 26, 1997

[30] Foreign Application Priority Data

Dec. 20, 1995 [CH] Switzerland .............................. 3605/95
Aug. 8, 1996 [CH] Switzerland .............................. 1950/96

[51] Int. Cl.[7] ....................................................... A61F 5/00
[52] U.S. Cl. .................................... 602/5; 602/6; 602/46; 602/21; 602/22
[58] Field of Search .................................. 602/5, 8, 46, 6, 602/21, 22; 59/35; 413/8; 414/1; 29/17.1

[56] References Cited

U.S. PATENT DOCUMENTS

| | | |
|---|---|---|
| 2,273,028 | 2/1942 | Eaton . |
| 2,667,868 | 2/1954 | Smyth . |
| 3,850,167 | 11/1974 | Seeley . |
| 4,161,175 | 7/1979 | Bentele . |

FOREIGN PATENT DOCUMENTS

| | | |
|---|---|---|
| 666752 | 12/1966 | Belgium . |
| 1123826 | 8/1968 | United Kingdom . |

*Primary Examiner*—John G. Weiss
*Assistant Examiner*—Kelvin E Hart
*Attorney, Agent, or Firm*—Tarolli, Sundheim, Covell, Tummino & Szabo L.L.P.

[57] ABSTRACT

With a medical splint (1) for securing and immobilizing movable body parts, in particular extremities of a human or an animal, along a splint axis (6), where said splint (1) comprises a sheet metal (2) that can be shaped plastically by hand and is covered on both sides with a cover layer (3, 4), a high shapability and stiffness at the same time are achieved by the fact that the sheet metal (2) is designed with corrugations in at least some areas, where the peaks and valleys of the corrugations (42) run essentially across the splint axis (6).

26 Claims, 7 Drawing Sheets

MEDICAL SPLINT, METAL SHEET FOR SUCH A SPLINT AND ITS USE

TECHNICAL FIELD

The present invention concerns the field of medical splints for human and veterinary medicine. It concerns a medical splint for securing or immobilizing movable body parts, in particular extremities of a person or animal along the axis of a splint, where said splint comprises a sheet metal or a plate that can be shaped by hand and is covered on both sides with a covering or cover layer.

Metal splints are not unusual. Such a splint is know, for example, from U.S. Pat. No. 3,943,923.

STATE OF THE ART

Many variations of splints consisting essentially of a metal plate (usually aluminum) that can be shaped easily and is covered on both sides with a cover layer of plastic foam, etc., are known in the state of the art. The splints are usually in the form of flat sheets which, when used, are adapted to the extremities to be splinted by plastic bending, although to a limited extent, to provide the required support and permit the required immobilization. The sheet metal on the inside may then either fill out practically the entire area of the splint, as is the case in U.S. Pat. No. 3,943,923, U.S. Pat. No. 4,676,233 or European Patent No. B1 39,323, or it is embedded in the splint in the form of several reinforcing metal strips, as is the case in European Patent No. B1 73,772.

Simultaneously fulfilling contradictory requirements with such adjustable or shapable splints presents problems: first, the splint must permit plastic deformation or bending with sufficient ease, so that it can be adapted by hand to the extremities (body parts) to be immobilized without any additional aids. Second, however, despite the easy deformability, the splint should be rigid enough to guarantee the required immobilization of the extremities.

To achieve the required stability of the splint, U.S. Pat. No. 4,161,175, for example, has proposed that ribs running back and forth in a straight line in the direction of the splint axis or a sinusoidal pattern be molded into the sheet metal to reinforce it. In U.S. Pat. No. 4,676,233, a similar reinforcement is produced by subsequent bending of a rib running in the axis of the splint.

An even greater problem is that because of the very low extensibility and compressibility [of the sheet metal] in the plane of the sheet at normal forces, it is very difficult to properly shape smooth sheet metal by plastic bending to conform to the irregular and sometimes sharply curved contours of the extremities or body parts to be immobilized or secured. Such shaping is especially difficult when the splint has a large, simply coherent area. This problem is not solved by the previously known splits using sheet metal. Instead, good adaptation to the complex shapes of extremities and body parts has been achieved so far only through traditional plaster splints or thermally molded plastic splints.

DESCRIPTION OF THE INVENTION

The object of the invention is therefore to create a medical splint that can easily be adapted by hand to the extremities or body parts to be secured by applying very little force starting from the shape of a flat sheet, that will have the required rigidity when shaped and is still flexible in use.

This object is achieved with the splint of the type defined initially by the fact that the sheet metal or plate is designed with corrugations at least in some areas, where the peaks and valleys of the corrugations run essentially across the splint axis.

The core of this invention consists of producing an easy extensibility and compressibility in the plane of the splint through corrugation of the sheet metal, so that the splint can be adapted to local irregularities in the extremities or body parts to be secured without any major problems. If local elongation is required, the corrugations in the sheet metal expands in this area. However, if local compression is necessary, the corrugations become steeper and closer together in this area. The splint thus has an extremely high local deformability. Another important feature of the splint according to this invention is the orientation of the corrugations across the splint axis. When the splint is applied with the splint axis parallel to the extremities (body parts) to be immobilized and the splint is bent around the extremities in a U shape, for example, across the splint axis to adapt it to the extremities, the special orientation of the corrugations according to this invention yields a surprisingly strong reinforcement of the splint after bending, so that a high shapability and good immobilization (splinting) are achieved at the same time with the corrugated sheet metal.

A first preferred embodiment of the splint according to this invention is characterized in that the sheet metal is designed to be corrugated over the entire area, and the corrugations are designed so they run continuously across the splint axis between opposing edges of the sheet metal. This permits flexible use of the splint for a wide variety of splinting applications.

According to another preferred embodiment, the splint has especially favorable shaping and securing properties when the sheet metal is made of aluminum and is 1 mm thick or less, preferably 0.3 mm or less, the corrugations have a periodic spacing of a few millimeters, preferably between 1 mm and 8 mm, in particular approximately 3–5 mm, and the corrugations have a peak-to-valley height of a few millimeters, preferably between 0.5 mm and 5 mm, in particular between 1 mm and 3 mm.

For cushioning and to increase wearing comfort, it has proven especially advantageous if, with the splint according to another preferred embodiment, the cover layers consist of a plastic, especially a foam, preferably an elastic polyethylene or polyurethane foam which may have a layer thickness of 1 to 3 mm, for example. Of course, in certain applications, the cushioning may also be much thicker (e.g., in the cm range). To further increase wearing comfort, a layer of textile may also be laminated to the outside of one or both cover layers.

The sheet metal can be embedded easily and reliably between the cover layers if, according to another preferred embodiment, the cover layers project beyond the edge of the sheet metal and form a peripheral edge area where the two cover layers are joined together, preferably bonded by gluing or welding.

According to another embodiment, it is advantageous for the splint to have an essentially rectangular edge contour for general applications as a forearm splint, etc.

According to another embodiment, it is advantageous for the edge contour of the splint to be adapted to the respective area of application for special applications, e.g., as a finger splint (metacarpal splint), a thumb splint or a forearm support.

Another preferred embodiment of the splint according to this invention is characterized in that devices for permanent or detachable connecting of the splint are provided with additional fasteners at one or more locations on the splint. In this way the splint can be additionally secured and set easily and flexibly by means of additional fasteners such as straps after shaping to the extremities.

In this connection, it has proven especially appropriate if the connecting devices include a pushbutton or a pushbutton part mounted in the plane of the splint.

The splint according to this invention can preferably be used as a forearm or wrist splint, a thumb splint, a finger splint or a leg and/or foot splint in humans.

A preferred embodiment of the splint according to this invention in the form of a finger splint for immobilizing one or more injured fingers with an elongated plate bordered in the longitudinal direction by two longitudinal edges is characterized in that the plate has side sections that are bordered by longitudinal edges and can be bent up out of the plane of the plate to serve as side walls to provide lateral support for the finger supported in the finger splint while at the same time making a contribution to the longitudinal stiffness of the finger splint, and several corrugations extending laterally from the longitudinal edges into the side sections or side walls are formed in the side sections of the plate.

Additional embodiments are derived from the dependent claims.

BRIEF EXPLANATION OF THE INVENTION

Figure 3:
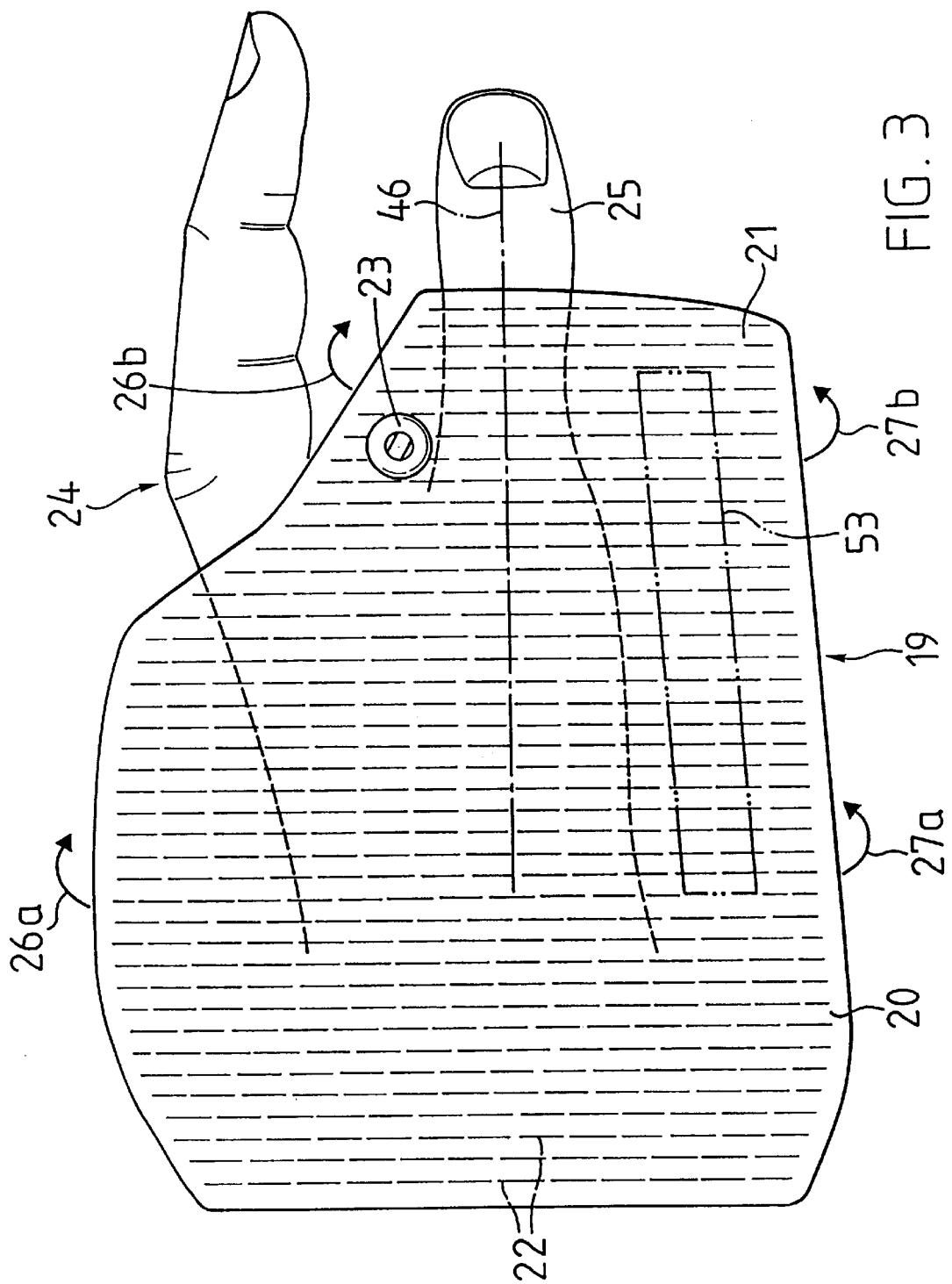
Figure 4A:
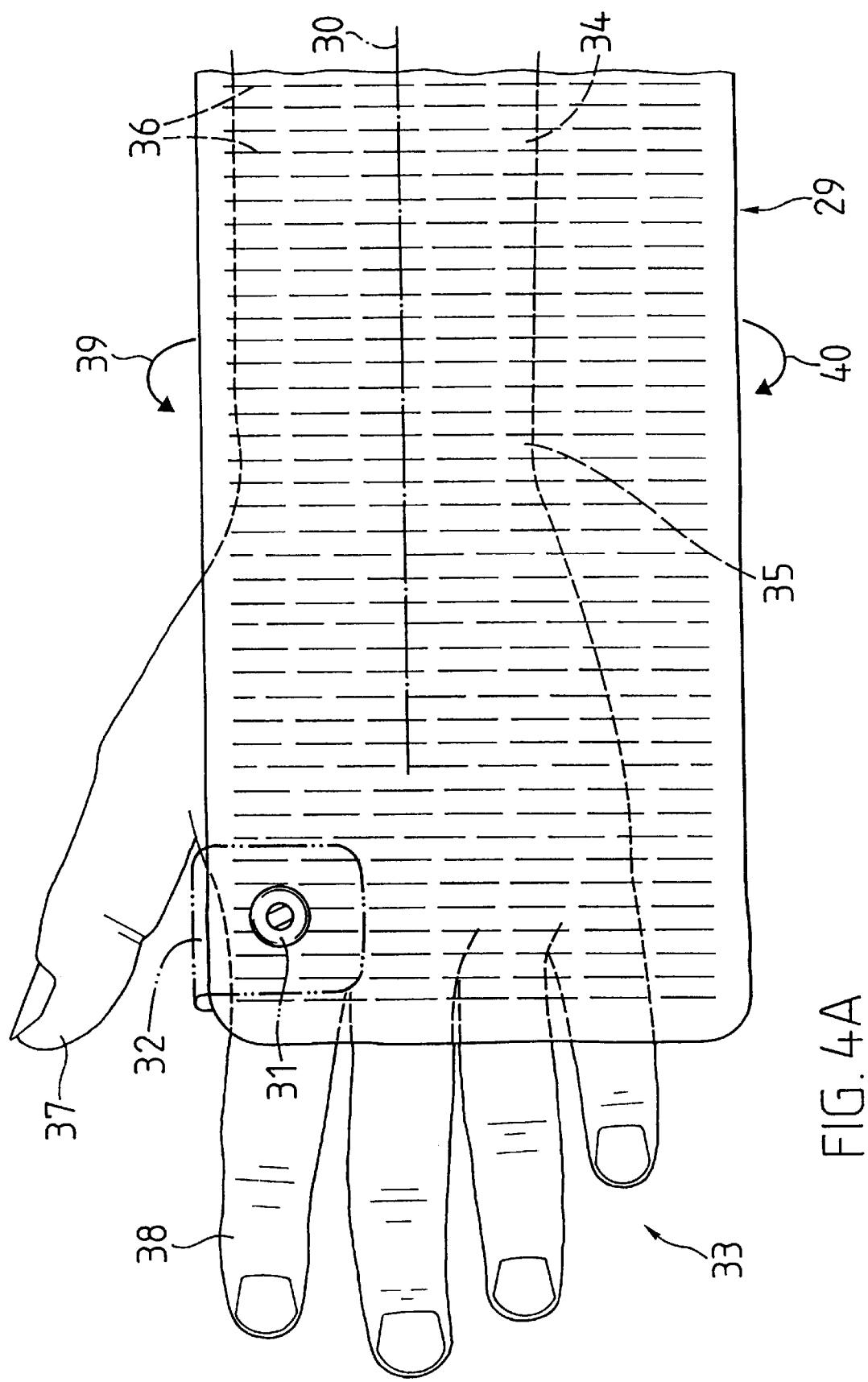
Figure 4B:
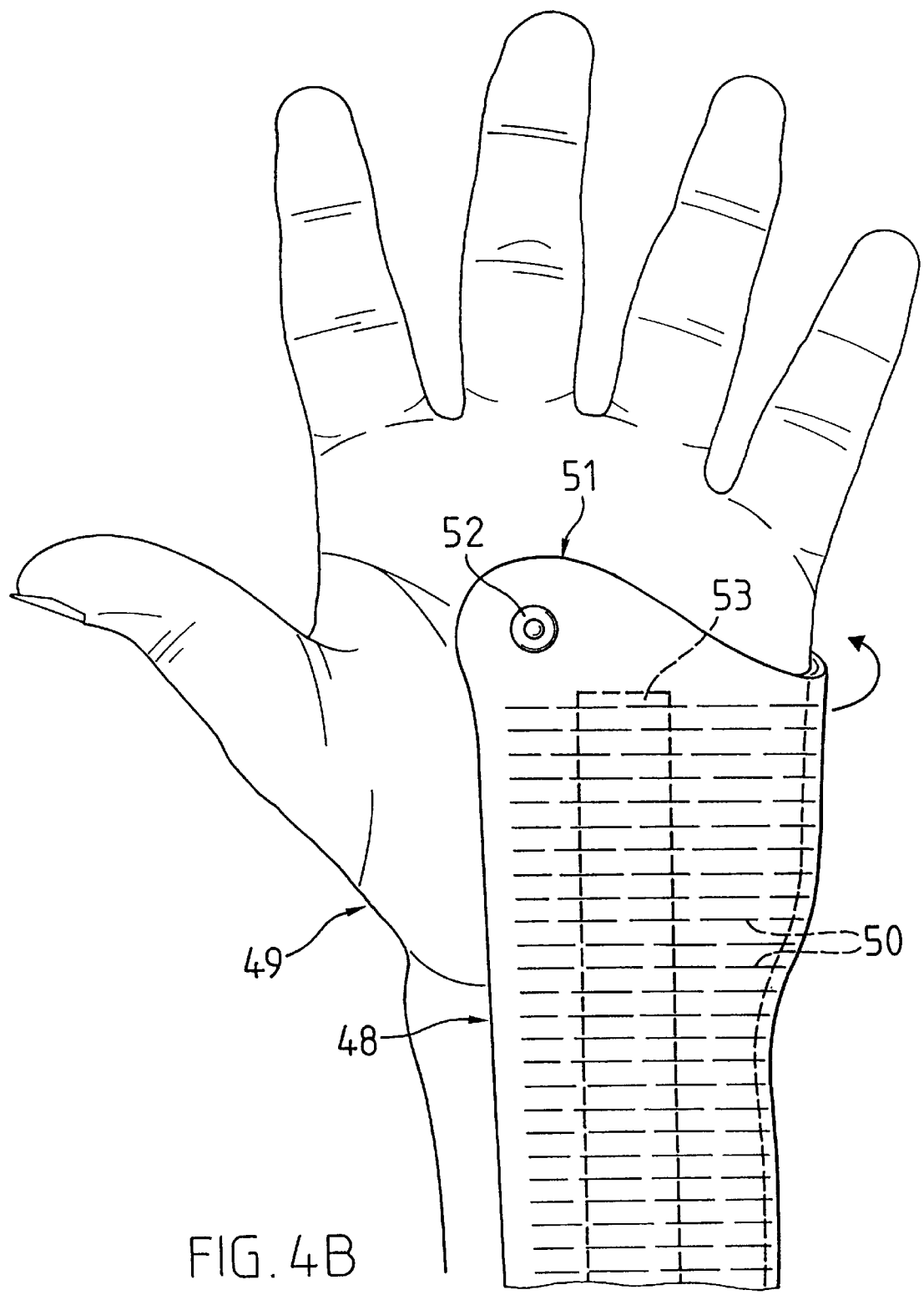
Figure 5:
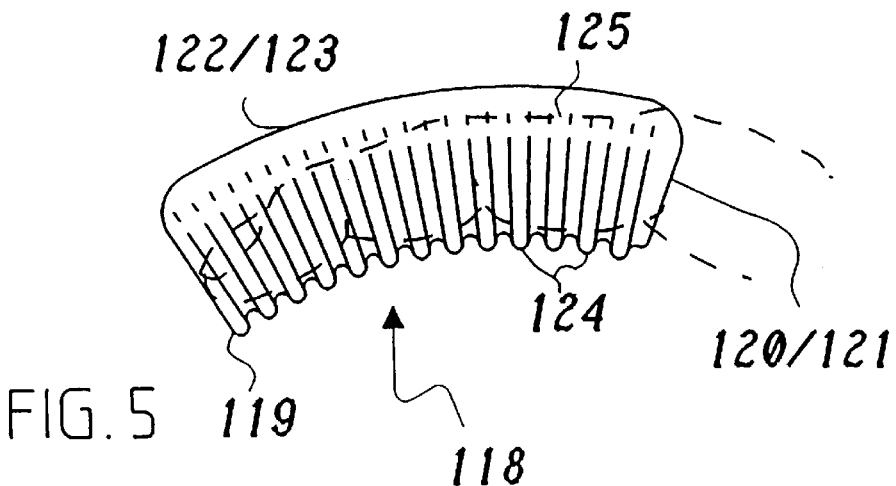
Figure 6A:
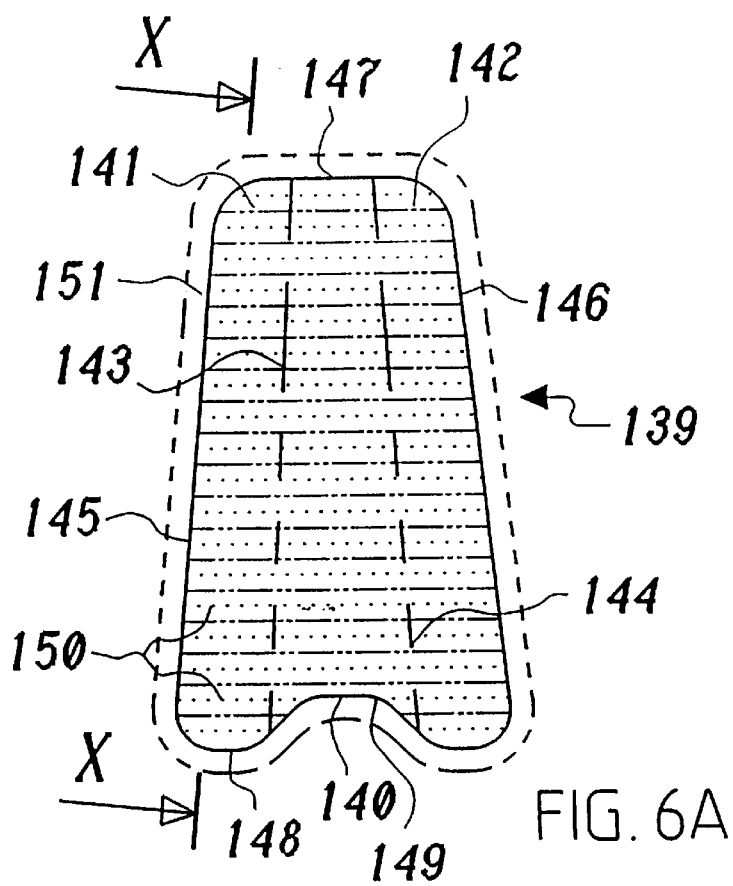
Figure 6B:
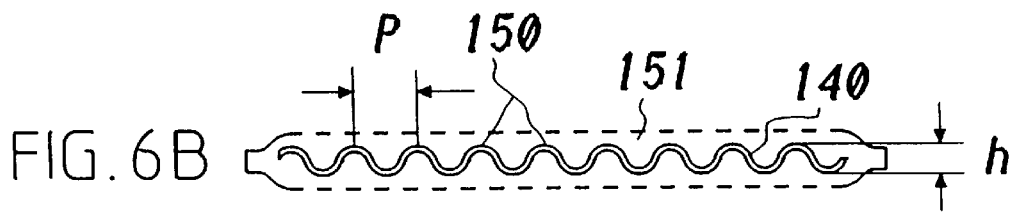
Figure 8:
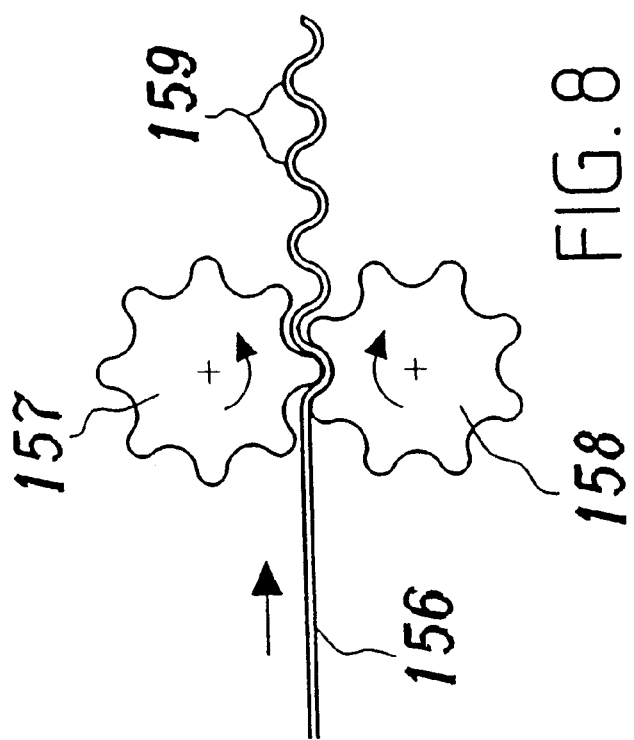
Figure 7:
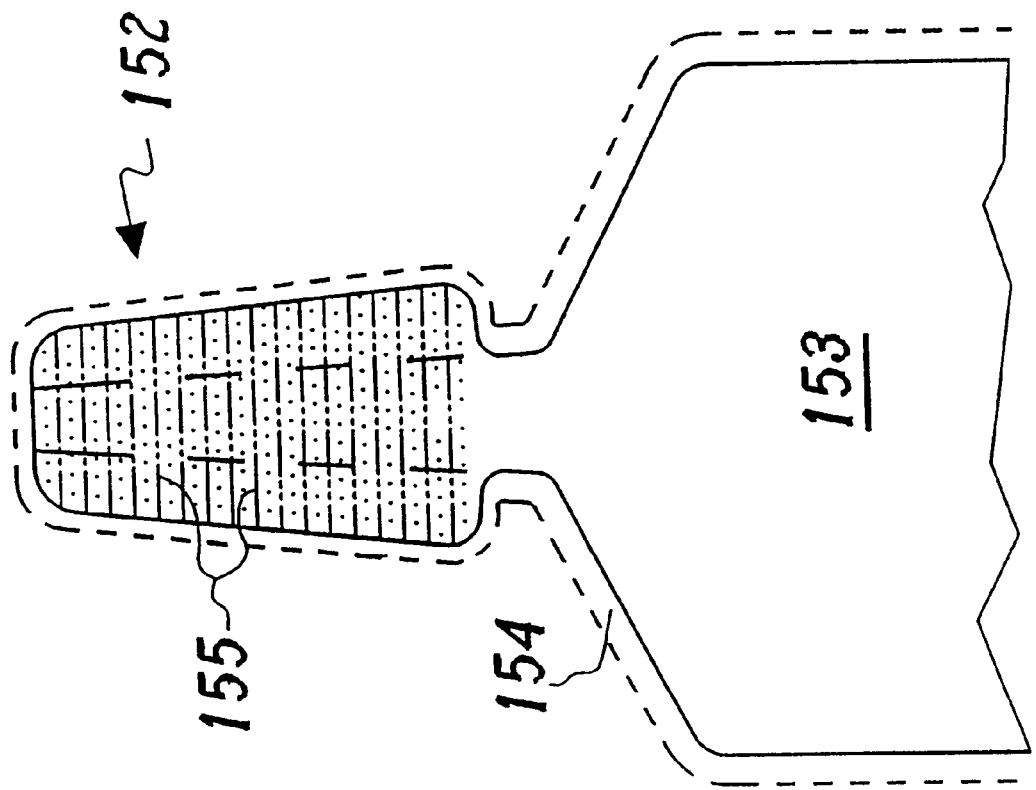

The invention is explained in greater detail below on the basis of embodiments in conjunction with the figures, which show:

FIG. 1: a preferred embodiment of a splint according to the invention in the generally applicable rectangular shape in a perspective view (A) and in a longitudinal section (B);

FIG. 2: an embodiment of a splint according to the invention, designed as a special finger splint (metacarpal splint) (A) and an additional fastener (B) designed as a strap for the finger splint (or splint forms);

FIG. 3: an embodiment of the splint according to the invention provided with a special edge structure for use as a thumb splint with immobilization of the wrist;

FIGS. 4A, 4B: use of a splint according to the invention as a support or splint for the forearm and wrist;

FIG. 5: a side view of one embodiment of a splint (curved in a trough shape) according to the invention as a finger splint with continuous corrugations;

FIG. 6: a top view (A) and a longitudinal view (B) of an unshaped plate for a finger splint of the type illustrated in FIG. 5;

FIG. 7: a top view of a finger splint according to FIG. 6 as a (integral) part of an arm splint; and FIG. 8: a schematic diagram of a process for producing the corrugated plate of a finger splint according to FIGS. 5 through 7.

METHODS OF EMBODYING THE INVENTION

Figure 1A:
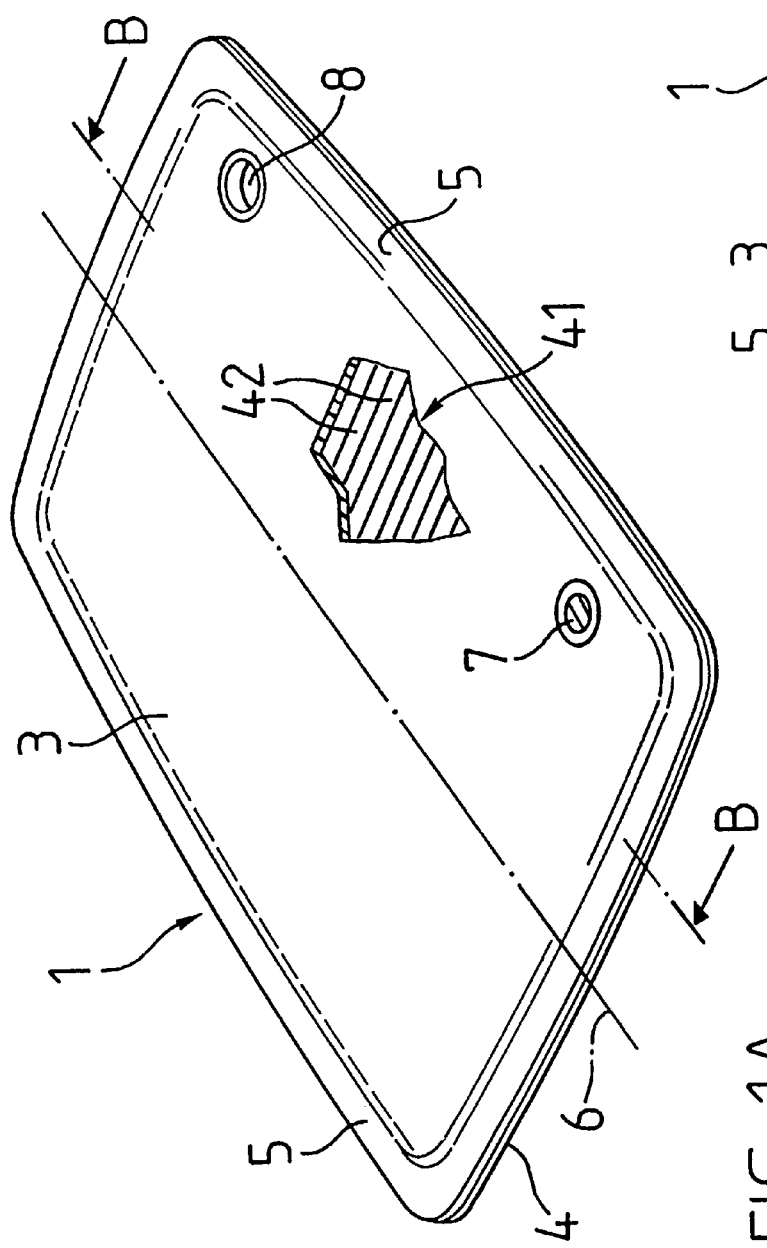

FIG. 1 shows a preferred embodiment of a splint according to this invention in a generally applicable rectangular shape. FIG. 1A shows a perspective view of the splint. FIG. 1B shows a longitudinal section through the splint along line B—B in FIG. 1A. Splint 1 in this embodiment has an elongated rectangular shape with preferably rounded corners. A central component of splint 1 is a thin sheet metal 2 of aluminum provided throughout with a fine corrugation (corrugations 42 in the cutaway view 41 in FIG. 1A). The outside dimensions of splint 41 may vary greatly. For example, a splint 1 with a width of 10–20 cm and a length of 20–30 cm is suitable as a general forearm splint.

Different dimensions are of course also conceivable. Furthermore, it is also conceivable to provide the splint with means for adjusting the shape, such as recesses, cutouts, projections, etc. It is also conceivable and advantageous to provide reinforcements, e.g., in the form of inserted metal strips or plates in certain areas of the splint having an increased supporting effect. It is also conceivable to reinforce the splint in some areas by changing the direction of the corrugations in those areas, in particular at right angles to the predominant direction of the corrugations. In use, the longitudinal axis of splint 1 also forms splint axis 6 which is oriented essentially parallel to the extremity to be immobilized, e.g., an arm.

The corrugation of sheet metal 2 is very small in comparison with the external dimensions: the periodic spacing P of corrugations 42 amounts to only a few millimeters. It is preferably between 1 mm and 8 mm and is especially approximately 3–5 mm. Corrugations 42 likewise have a peak-to-valley height of a few millimeters, preferably between 1 mm and 8 mm, especially between 2 mm and 5 mm. Aluminum sheet metal 2 is 1 mm thick or less, preferably 0.3 mm thick or less. Corrugations in sheet metal 2 may be produced, for example, by pulling a flat sheet metal through two contra-rotating, intermeshing gearwheel rollers or pressed between two suitably corrugated molds. Although corrugated sheet metal with the stated values has proven especially suitable, it is fundamentally conceivable for other dimensions to be used.

Corrugated sheet metal 2 per se could essentially be used as a splint. For cushioning and thermal insulation (metal feels cold on the skin) sheet metal 2 inside splint 1 is covered with a cover layer 3 or 4 on both sides. A textile fabric, felt, etc., can be used as the cover layer. However, cover layers 3, 4 are preferably made of a plastic, especially a foam, preferably an elastic polyethylene or polyurethane foam a few millimeters thick, that is flexible, elastic and hygienically safe. As FIG. 1B shows, cover layers 3, 4 project beyond the edge of sheet metal 2. They form a uniform peripheral edge area 5 in which the two cover layers 3, 4 are joined together, preferably bonded by gluing or welding. At the same time, cover layers 3, 4 are bonded on the inside to sheet metal 2 (e.g., by welding). Cover layers 3, 4 thus form a closed wrapping that holds the corrugated sheet metal 2 and surrounds it on all sides.

When used, splint 1 is applied with splint axis 6 parallel to the extremity (arm, etc.) or body part (neck, torso) and is adjusted and shaped to the extremity (body part) by bending in a U shape across the splint axis (see also FIGS. 4A, 4B). The splint need not necessarily be in the form of a flat sheet, but may also be preshaped in a trough shape to facilitate use and prevent an incorrect orientation in use. Corrugation of sheet metal 2 permits local compression or elongation in the plane of sheet metal 2 in a simple way, so that the splint can also easily be adapted by hand to extremities (body parts) with a very irregular shape.

At the same time, the special orientation of corrugations 42 running continuously across splint axis 6 from one edge of sheet metal 2 to the other edge surprisingly ensures that splint 1 will have an unusually high rigidity after bending, although it is initially very flexible before bending. In particular, a local increase in rigidity can be achieved by flattening the corrugations in this area with a thumb or otherwise or pushing them out of the sheet. Despite the rigidity achieved due to the bending, the splint remains surprisingly shapable, so that it can also be adapted to the body part or extremity again at any time.

In the shaped, bent form, the splint can be attached to the splinted extremity (body part) with additional fasteners such as a strap (FIG. 2B) or similar device to reliably prevent the splint from falling off. To permit a detachable connection of such fasteners to the splint, connecting devices may be provided at suitable locations on splint 1 (e.g., in corner areas). According to FIG. 1A, the connecting devices may be pushbuttons or pushbutton parts 7 or eyes 8, for example. However, it is also conceivable to provide different connecting devices such as adhesive surfaces or Velcro-type fasteners or hooks. If eyes 8 are used, they are attached in the plane of the splint through the sequence of layers of bottom cover layer 4, sheet metal 2 and top cover layer 3. However, pushbuttons or pushbutton parts 7 are preferred, projecting only through sheet metal 2 and one of cover layers 3, 4, but covered by the other cover layer on the back. The particular advantage of pushbuttons is that they permit rotation of the fasteners after connection to the splint. In this way the fasteners can be attached optimally to the splinted body part.

Figure 2A:
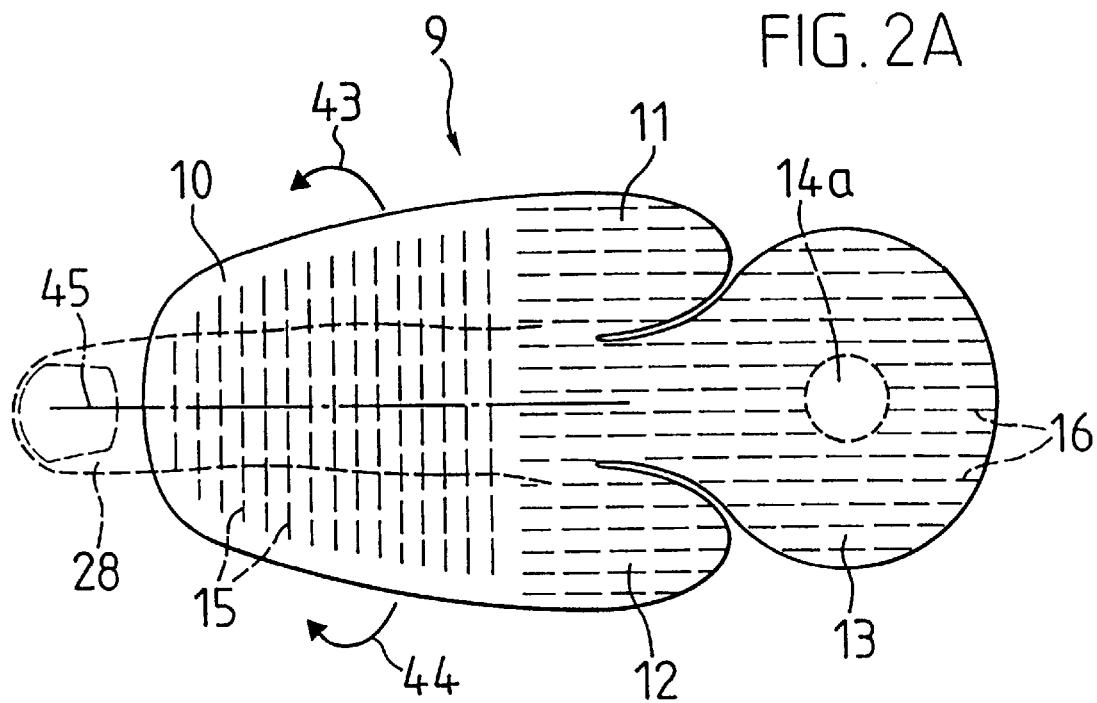

FIG. 2A shows a second very special embodiment in the form of a finger splint (metacarpal splint). Splint 9 consists of several interconnected subareas, namely a finger part 10 that tapers toward the front end and has connected to it two tab-like supporting parts 11 and 12 at the sides toward the rear and a supporting disk 13 in the middle. Like splint 1, splint 9 is constructed as a series of layers, the bottom cover layer, the corrugated sheet metal and the top cover layer. The corrugations of the sheet metal are indicated by parallel lines which are shown as dotted lines. In the front finger part 10, corrugations 15 run across splint axis 45. Thus the splint can be bent in a U shape as described above in the direction of arrows 43 and 44 around a finger 28 (shown with dotted lines) which is lying on splint 9 and is to be splinted. In particular, corrugations 15 make it possible for finger part 10 to be curved after bending in the direction of splint axis 45, so that splinted finger 28 is secured in a preferred curved position. Finger part 10 may end before the finger tip, as shown in FIG. 2A, but it may also be longer than the finger to be splinted.

In the area of supporting parts 11, 12 and supporting disk 13, corrugations 16 in the sheet metal are oriented parallel to splint axis 45. As a result, these parts which support finger part 10 on the palm of the hand have an increased stability. However, these parts may also be reinforced by an additional sheet, so the thickness of the splint is a multiple of the usual thickness in these areas. To attach finger splint 9 to the hand, a strap 17 may be detachably attached to the splint according to FIG. 2B. Strap 17, which is made of an elongated strip 18 of foam or fabric, etc., is preferably finished with a pushbutton part 14b at one end. In this area, strap 17—if it is used together with splints 19 or 29 according to FIG. 3 or 4—may also be provided with an insert 47 of a reinforcing, plastically deformable material, e.g., aluminum sheet metal which is also corrugated. Likewise, as an alternative, an intermediate piece made of a relatively rigid, plastically deformable material that is provided with pushbutton parts at both ends and is attached to the splint at one end and to strap 17 at its other may also be provided between strap 17 and splint 9.

The other pushbutton part 14a as the counterpart piece is arranged at the center of supporting disk 13. When splint 9 is positioned in the palm of the hand and is shaped in finger part 10 to conform to finger 28 which is to be splinted, strap 17 (or the above-mentioned intermediate piece with the following strap) is pressed with pushbutton part 14b into pushbutton part 14a so it engages, and strap 17 is wrapped several times around the hand and secured with adhesive tape or the usual hooks, for example. Splint 9 is thus be secured reliably on the hand.

Another embodiment illustrated in FIG. 3 shows a splint 19 with a special (non-rectangular) edge contour which is used especially as a thumb splint. In this case, splint 19 comprises a wide wrist part 20 followed by a narrower, tapering thumb part 21. However, the splint may also be designed so it is shorter and has no wrist part, in which case it then serves as a pure metacarpal-thumb splint, where the wrist can move freely. The internal structure of splint 19 is the same as that of splint 1 in FIG. 1. Sheet metal corrugations 22 (not visible from the outside because of the cover layers) are indicated by the parallel dotted lines. In this case, corrugations 22 are arranged continuously across splint axis 46. Splint 19—as shown in FIG. 3—is placed on the side of hand 24 to be splinted so that thumb part 21 with splint axis 46 is parallel with thumb 25. Thumb part 21 may leave the tip of the thumb free, as illustrated in FIG. 3; however, it may also completely cover the length of thumb 25. Splint 19 is then bent in the direction of arrows 26a,b and 27a,b and shaped to conform to hand 24. Thumb 25 is then secured with respect to hand 2 so that the base of the thumb is immobilized. In addition, the wrist can also be secured (immobilized) by an extension of splint 19 toward the forearm. Furthermore, it may be advantageous to embed a reinforcement 53 in certain areas of splint 19, e.g., in the form of a strip running parallel to splint axis 46 (see also FIG. 4B). Then after adjusting splint 19 to conform to thumb 25, this reinforcement assures that it will be secured even better. To attach splint 19 to the hand, connecting devices in the form of an embedded pushbutton part 23 are again provided in the area of splint 19, which comes to lie between thumb 25 and the index finger, so that a strap, for example, according to FIG. 2B (or a corresponding intermediate piece) may be snapped into it.

Another application is the splinting of the forearm as illustrated in FIG. 4A or supporting the wrist, which may be necessary in the case of tendinitis or surgery, for example. Splint 29, which in this case has practically the general rectangular shape of splint 1 according to FIG. 1 in addition to having the same internal structure, is placed on forearm 34 in the manner illustrated here so that it projects beyond wrist 35 and the base of the finger but leaves the finger itself mostly free. Then the splint is bent in the direction of arrows 39, 40 around forearm 34, wrist 35 and hand 33 in a U shape, where sheet metal corrugations 36 in the splint running continuously across splint axis 30 ensure the shapability and reinforcement of the splint. To attach splint 29 to the hand 33 or forearm 34, here again a pushbutton 31 or similar device may be provided as a connecting device into which a strap according to FIG. 2B or a supporting part 32 may be snapped. Supporting part 32 may be in particular a small splint having the same design with a corrugated sheet metal as splint 29 and bent in a hook shape through the wedge between thumb 37 and index finger 38, thus securing splint 29 on hand 33. However, splint 29 may also be secured by a buttoned band wrapped several times around the arm according to FIG. 2B.

Figure 2B:
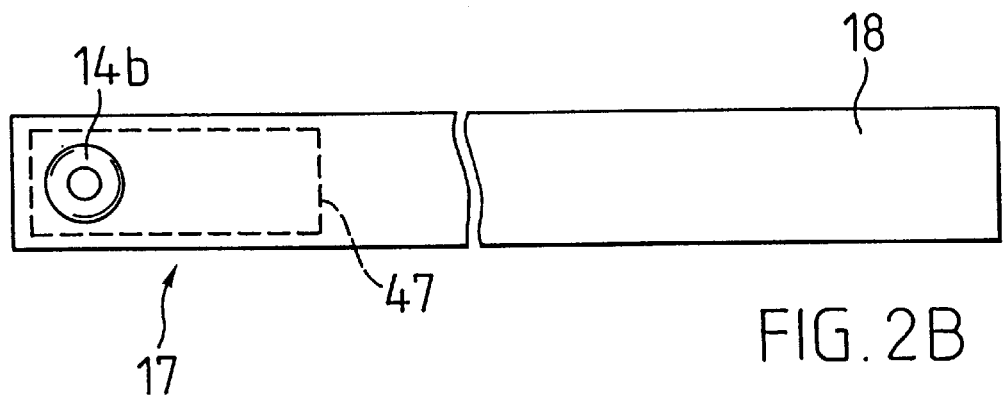

Furthermore, a strap according to FIG. 2B may be attached to the free end of supporting part 32. However, it is equally conceivable for supporting part 32 to be designed as an integrally molded extension of splint 29 projecting at the side, so that the splint can be attached to a hand 33 without a pushbutton and without additional separate fasteners. The same principle (of the integrally molded extension) may of course also be used in conjunction with thumb splint according to FIG. 3.

Another embodiment is splint 48 illustrated in FIG. 4B in the form of a shortened forearm and wrist support. Splint 48 has an essentially rectangular shape with corrugations 50 running across it and an integrally molded "eye" 51 in which a pushbutton 52 is arranged as a fastener, e.g., for a band according to FIG. 2B. Splint 48 is bent in a U shape around the wrist of hand 49 in the illustrated manner (arrow) so the wrist is secured but the fingers can move freely. Splint 48 can then be secured on the wrist with a buttoned band according to FIG. 2B which is first passed between the thumb and index finger and then wrapped several times around the splinted wrist. In addition, to increase the stability of splint 48 in the area of the wrist, a reinforcement 53 in the form of a thicker inserted strip (shown with dotted lines in FIG. 4B) may also be provided so that it runs parallel to the forearm over the wrist and is welded or glued into the cover.

On the whole, this invention yields a splint that can be shaped easily and adapted to the extremities or body parts to be splinted, has a surprisingly good shapability despite its high rigidity (after shaping) and can be adapted in a flexible manner to various applications. Especially advantageous applications include arm splints, hand splints or finger splints. However, it is also conceivable to use this as a splint in the area of the leg or foot or in other areas of the human body (neck, spine, etc.) or even on animals.

FIG. 5 shows a side view of one embodiment of a splint according to this invention in the form of a finger splint. For the sake of simplicity, the usual covering on this finger splint in the form of an elastic material, e.g., a layer of polyethylene foam or polyurethane foam, is omitted here. Finger splint 118 from FIG. 5 consists essentially of an elongated plate 119 made of sheet aluminum or aluminum foil that has been bent in a trough shape in the longitudinal direction and can be adapted to the length of a finger 125. The bending results in two side walls 120 and 121 that [provide] lateral support for finger 125 which is to be secured and rests on plate 119 in the middle area and at the same time imparts longitudinal stiffness to the finger splint. The splint, which is at first straight in the longitudinal direction, is then usually curved to make it possible to secure finger 125 in a relaxed curved position (so-called physiological position). The curvature is such that elongation takes place in the longitudinal direction in the area of longitudinal edges 122, 123 of plate 119 which also border side walls 120, 121 at the top. To permit such elongation, corrugations 124 are provided as elongating devices in plate 119 of finger splint 118.

A finger splint 139 according to FIG. 5 with corrugations 150 for elongation is shown in a bent state in a top view in FIG. 6A. Finger splint 139 from FIG. 6A consists essentially of a plate 140 that is bordered by longitudinal edges 145, 146 and transverse edges 147, 148 and is enclosed by a corresponding cover 151. Intended bending lines 143, 144 form the dividing lines for side sections 141, 142, which are to be bent out of the plane of the plate to form side walls of the splint, to ensure the longitudinal stability and to provide lateral support for the finger(s). In this embodiment, corrugations 150 are provided as the means of elongation, running across the longitudinal direction of plate 140 from one longitudinal edge 145 to the other longitudinal edge 146, as indicated by dotted lines and dash-dot lines in FIG. 6A.

In this example, plate 140 has a width that decreases toward the front, taking into account the shape of the finger which becomes narrower toward the tip, with the result that the bent side walls (120, 121 in FIG. 5) can retain an approximately constant height despite the varying thickness of the finger. However, a constant width can also be selected, e.g., to achieve simplified handling of the plate in manufacture. Plate 140 is preferably rounded at the corners to reduce the danger of injury. Plate 140 is also covered by a covering 151, forming a "pocket" that is closed on all sides for plate 140 as indicated by a dotted line in FIG. 6. Such a covering in the form of an elastic foam layer is described in detail in U.S. Pat. No. 4,676,233, for example, so that further explanation may be omitted here. However, it should be pointed out that here again, other materials such as plastic films, paints and varnishes or textiles are also suitable coverings.

It is self-evident that the intended bending lines 143, 144 may have a different location and a different course, depending on the shape of the finger to be secured, or they may even be omitted if the side walls are bent up smoothly—as is the case with the splint bent preferably in a trough shape. To prevent plate 140 from pressing against the base of the finger, an indentation 149 is preferably provided on the rear transverse edge 148 of plate 140.

The longitudinal section through finger splint 139 along line X—X in FIG. 6A is illustrated in FIG. 6B, which shows that plate 140 is designed as a corrugated plate, preferably with continuous corrugations in the longitudinal direction, where corrugations 150 have a period P and a height h (between the peaks and valleys of the corrugations). Since corrugations 150 provide reinforcement for plate 140 in the transverse direction and thus essentially hinder the bending of side sections 141, 142, the material and thickness of plate 140 and the geometry of the corrugations must be selected suitably to permit sufficiently easy shaping of the finger splint for use. It has proven suitable for plate 140 to be made of aluminum if plate 140 is 0.5 mm thick or less, preferably 0.2 mm thick or less, if the corrugations have a periodic spacing P of a few millimeters, preferably between 0.5 and 5 mm, especially approximately 2–3 mm, and if the corrugations have a height h of a few millimeters, preferably between 0.5 mm and 5 mm, preferably between 1 mm and 3 mm. Especially aluminum plates or sheets approximately 0.2 mm thick or less guarantee good shapability and, at the same time, stability of the finger splint.

When a finger splint according to FIG. 6 with a corrugated plate is bent in a trough shape and then curved in the longitudinal direction, this yields the condition illustrated in FIG. 5. Finger splint 118 with corrugated plate 119 encloses finger 125 with side walls 120 and 121. The curvature of the splint in the longitudinal direction results in a strong tensile stress at longitudinal edges 122 and 123 of plate 119, smoothing out corrugations 124 in the area of the longitudinal edges decreasingly toward the inside, so that with an extreme curvature, the corrugations disappear completely at longitudinal edges 122, 123 and the straight longitudinal edges illustrated in FIG. 5 develop. With the smoothing of the corrugations, side walls 120, 121 are also reinforced at the same time, so that in this case the essentially opposite requirements of extensibility and rigidity are met simultaneously in an optimum manner.

It is advisable to keep finger splints of the type illustrated in FIGS. 5 and 6 in an unbent state so that they can be packaged and stored easily (like surgical dressings, etc.). It is essentially also conceivable to keep different sizes of splints for different finger sizes. However, it has been found that all essential applications can be covered with one standard size as long as a single finger is splinted. With such a standard size, plate 119, 140 has a maximum width between 4 cm and 10 cm, preferably approximately 6 cm, and a maximum length between 6 cm and 14 cm, preferably approximately 10 cm. Projecting areas of the splints can be bent back. If the splints are provided for simultaneously splinting several fingers side by side in one splint, the plates must be selected with a greater width accordingly. It is also conceivable for finger splint 152 to be an integral part of a longer and wider arm splint 153, as illustrated in FIG. 7, and to be integrally molded on the front end of arm splint 153. In this way it is possible to secure the finger relative to the hand and the arm in the case of injuries to the base of the finger, so that undisturbed healing is also possible in this case. Here again, cushioning of splints 152 and 153 by a covering 154 has proven expedient.

The finger splint with a corrugated plate according to FIGS. 5, 6 and 7 can be manufactured in various ways. It is especially simple to manufacture it, as illustrated in FIG. 8, by passing a flat plate 156 between two meshed gearwheels 157, 158 or toothed wheels in the direction of the arrow to produce corrugations 159. The completely corrugated plate can then be provided with the desired covering. However, the covering can also be applied before corrugating. The teeth of gearwheels 157, 158 may have different shapes. However, it is advantageous if the corrugations 159 thus produced form a uniformly curved wavy line to prevent notching effects in the plate that could cause the plate to break when bent and to facilitate the smoothing of the corrugations when bending the finger splint.

Instead of gearwheels, however, the plate may also be corrugated in various other ways. For example, it is conceivable for the corrugations to be produced by pressing the plate between suitably corrugated compression molds that either have flat mold faces and are pressed together at right angles or have curved mold faces and roll against each other. The compression molds may be designed so that they execute a punching and cutting function at the same time and provide the splint with the desired edge contour.

I claim:

1. A medical splint for securing and immobilizing movable body parts, in particular extremities, of a human or an animal along a splint axis, where said splint comprises a sheet metal or plate that is covered on both sides with a covering or a cover layer, characterized in that the sheet metal or the plate is designed so it is corrugated in at least some areas, where the peaks and valleys of the corrugations run essentially across the splint axis, said splint having an additional reinforcement provided in predetermined areas of said splint, in the form of an inserted strip or plate of sheet metal.

2. A medical splint for securing and immobilizing movable body parts, in particular extremities, of a human or an animal along a splint axis, where said splint comprises a sheet metal or plate that is covered on both sides with a covering or a cover layer, characterized in that the sheet metal or the plate is designed so it is corrugated in at least some areas, where the peaks and valleys of the corrugations run essentially across the splint axis, said splint being in the form of a finger splint for securing a single injured finger or several injured fingers with an elongated plate, bordered by two longitudinal edges in the longitudinal direction, said plate having side sections bordered by the longitudinal edges and such side sections can be bent out of the plane of the plate to form side walls to provide support on the sides for the finger held in the finger splint and at the same time contribute to the longitudinal stiffness of the finger splint, said side sections having several corrugations extending laterally from the longitudinal edges into the side sections or side walls.

3. Finger splint according to claim 2, wherein the corrugations are designed as continuous corrugations between the two longitudinal edges.

4. Finger splint according to claim 3, characterized by the plate being designed as a corrugated plate in at least some sections with the corrugations running continuously in the longitudinal direction.

5. Finger splint according to claim 4, characterized by the plate being made of aluminum, the plate being 0.5 mm thick or less, the plate preferably being 0.2 mm thick or less, the corrugations having a periodic spacing (P) of a few millimeters, preferably between 0.5 mm and 5 mm, in particular approximately 2–3 mm and the corrugations having a height (h) between the peaks and the valleys of a few millimeters, preferably between 0.5 mm and 5 mm, preferably between 1 mm and 3 mm.

6. Finger splint according to claim 2, characterized by the plate of the finger splint decreasing in width toward the front of said finger splint.

7. Finger splint according to claim 2, characterized by the plate of the finger splint having a constant width.

8. Finger splint according to claim 6, characterized by the plate having a maximum width between 4 cm and 10 cm, preferably approximately 6 cm, and a maximum length between 6 cm and 14 cm, preferably approximately 10 cm.

9. Finger splint according to claim 2 characterized by the plate being bordered at the rear by a rear transverse edge and having an indentation in the area of the rear transverse edge.

10. Finger splint according to claim 2 characterized by the covering being made of a foam material, preferably an elastic polyethylene foam or polyurethane foam.

11. Finger splint according to claim 2 characterized by said finger splint being part of a longer and wider arm splint and is integrally molded on the front end of the arm splint.

12. Process for manufacturing a finger splint according to claim 2, characterized by the flat plate passing between two meshed gearwheels or toothed rolls to produce the corrugations.

13. Process for manufacturing a finger splint according to claim 2, characterized by a flat plate being pressed between two suitably corrugated compression molds to produce the corrugations.

14. Process according to claim 13, characterized by the edge contour of the finger splint being punched and cut simultaneously with the compression molding process.

15. A medical splint deformable around movable body parts and for securing and immobilizing a movable body part of a human or an animal along a splint axis parallel to the body part and which body part is curved along said splint axis and transverse to said splint axis, said splint comprising a plate having a covering on both sides of said plate, said plate being deformable by hand to the shape of said body part and to the shape of local irregularities of said body part, said plate having a series of corrugations with peaks and valleys which extend transverse to said splint axis, the material and thickness of said plate and the geometry of said corrugations being selected such that certain portions of said corrugations are expandable and certain portions of said corrugations are contractible as said plate and covering are deformed without any additional aids to the shape of said body part and to the shape of said local irregularities of said body part.

16. A medical splint according to claim 15 wherein said plate has corrugations over its entire area, and the corrugations extend continuously across the splint axis between opposite edges of said plate.

17. A medical splint according to claim 15 wherein said plate is made of aluminum, said plate is 1 mm thick or less, preferably 0.3 mm thick or less, said corrugations have a periodic spacing (P) of a few millimeters, preferably between 1 mm and 8 mm, in particular approximately 3–5 mm, and said corrugations have a peak-to-valley height of a few millimeters, preferably between 1 mm and 8 mm, in particular between 2 mm and 5 mm.

18. A medical splint according to claim 15 wherein said covering is made of a elastic polyethylene foam or polyurethane foam.

19. A medical splint according to claim 15 wherein said covering extends beyond the edge of said plate and forms a peripheral edge area where two cover layers on opposite sides of said plate are joined together.

20. A medical splint according to claim 15 wherein the splint has an essentially rectangular edge contour.

21. A medical splint according to claim 15 further including a projection extending at the side of the splint for fastening the splint to the body part.

22. A medical splint according to claim 15 further including devices for connecting the splint with additional fasteners provided at one or more locations on the splint.

23. A medical splint according to claim 22 wherein said connecting devices comprise a pushbutton part embedded in the plane of the splint.

24. A medical splint according to claim 23 wherein said pushbutton part is covered on its back by said covering.

25. A medical splint according to claim 22 wherein said connecting devices comprise an eye embedded in the plane of the splint.

26. A medical splint according to claim 22 wherein said connecting devices comprise a Velcro-type fastener.

* * * * *